US012599514B2

(12) United States Patent
Moritani

(10) Patent No.: US 12,599,514 B2
(45) Date of Patent: Apr. 14, 2026

(54) DISPOSABLE DIAPER AND METHOD FOR MANUFACTURING SAME

(71) Applicant: DAIO PAPER CORPORATION, Ehime (JP)

(72) Inventor: Akie Moritani, Ehime (JP)

(73) Assignee: Daio Paper Corporation, Ehime (JP)

( * ) Notice: Subject to any disclaimer, the term of this patent is extended or adjusted under 35 U.S.C. 154(b) by 267 days.

(21) Appl. No.: 18/551,152

(22) PCT Filed: Mar. 4, 2022

(86) PCT No.: PCT/JP2022/009453
§ 371 (c)(1),
(2) Date: Sep. 18, 2023

(87) PCT Pub. No.: WO2022/244386
PCT Pub. Date: Nov. 24, 2022

(65) Prior Publication Data
US 2024/0189162 A1      Jun. 13, 2024

(30) Foreign Application Priority Data

May 20, 2021      (JP) ................................. 2021-085134

(51) Int. Cl.
*A61F 13/15*          (2006.01)
*A61F 13/49*          (2006.01)
(Continued)

(52) U.S. Cl.
CPC ...... *A61F 13/533* (2013.01); *A61F 13/49017* (2013.01); *A61F 2013/53445* (2013.01)

(58) Field of Classification Search
CPC .............. A61F 13/533; A61F 13/49017; A61F 2013/53445
(Continued)

(56) References Cited

U.S. PATENT DOCUMENTS 5,925,026 A * 7/1999 Arteman ........... A61F 13/53747
                                                      604/383
2010/0201024 A1* 8/2010 Gibson ............. A61F 13/15707
                                                      264/156
(Continued)

FOREIGN PATENT DOCUMENTS

EP          3508183 A1      7/2019
JP       2012-179220          9/2012
(Continued)

OTHER PUBLICATIONS

Extended European Search Report for European Patent Appl. No. 228043071, dated May 12, 2025.
(Continued)

*Primary Examiner* — Jacqueline F Stephens
(74) *Attorney, Agent, or Firm* — Andrus Intellectual Property Law, LLP

(57)                ABSTRACT

A disposable diaper whose absorber body changes its shape to motion of the wearer for enhanced fitting and wearing comfort, without excessively increased rigidity, includes an absorbent element having an absorber body and a wrapping sheet, and provided on its body side round and oval compressed areas, respectively. The round areas includes first and second compressed areas arranged respectively at intervals in the width and front-back directions, the second areas shifted from the first areas by half the intervals in the width and frond-back directions, the oval areas includes first compressed areas arranged between adjacent first round areas and between adjacent second round areas, with its major axis being aligned to the width direction, and second compressed areas, each arranged between first and second round areas with its major axis being aligned to a line connecting the first and second round areas.

7 Claims, 8 Drawing Sheets

(51) Int. Cl.
*A61F 13/533* (2006.01)
*A61F 13/534* (2006.01)

(58) Field of Classification Search
USPC ................................................. 604/379, 380
See application file for complete search history.

(56) References Cited

U.S. PATENT DOCUMENTS

| | | | |
|---|---|---|---|
| 2017/0128283 A1 | 5/2017 | Uda | |
| 2017/0312144 A1 * | 11/2017 | Moritani | ........... A61F 13/49406 |
| 2019/0159945 A1 * | 5/2019 | Tokunaga | ............. A61F 13/534 |
| 2019/0201247 A1 | 7/2019 | Tsukuda et al. | |

FOREIGN PATENT DOCUMENTS

| | | | |
|---|---|---|---|
| JP | 2014-117410 | 6/2014 | |
| JP | 2016010594 A | 1/2016 | |
| WO | 2012118235 A1 | 9/2012 | |
| WO | WO-2017091924 A1 * | 6/2017 | ......... A61F 13/5376 |
| WO | 2017/217355 | 12/2017 | |
| WO | 2018/042544 | 3/2018 | |
| WO | 2019/123781 | 6/2019 | |

OTHER PUBLICATIONS

International Search Report for PCT/JP2022/009453, dated May 17, 2022.

* cited by examiner

[FIG.1]
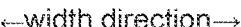
←width direction→
10
15
front-back
direction
A
50
51  52
12  11  60
32
30
31
40
41
30A
EF
20
EF
A
L1  L2
SF          20          SF

[FIG.2]
←width direction→
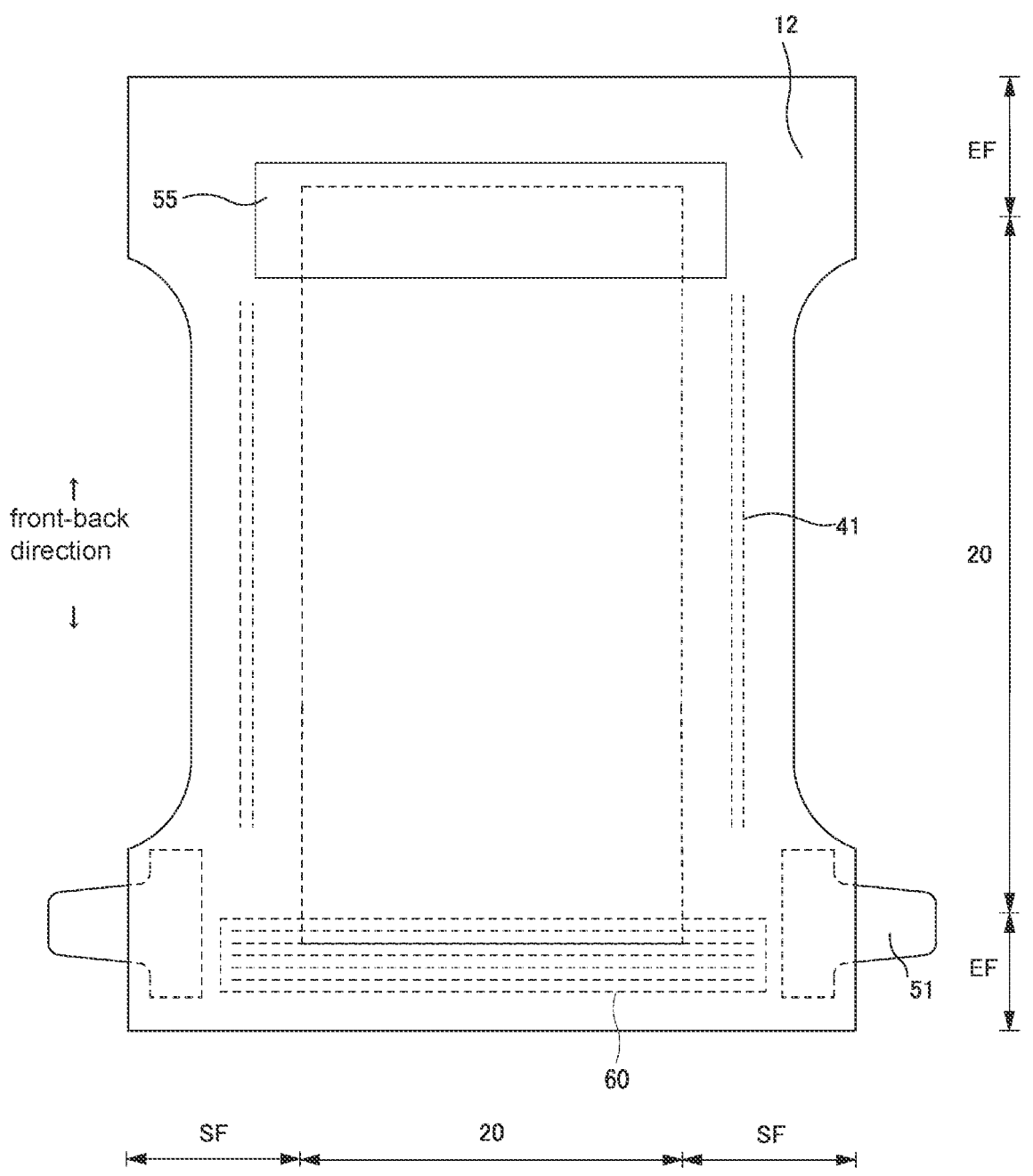
front-back
direction

[FIG.3]
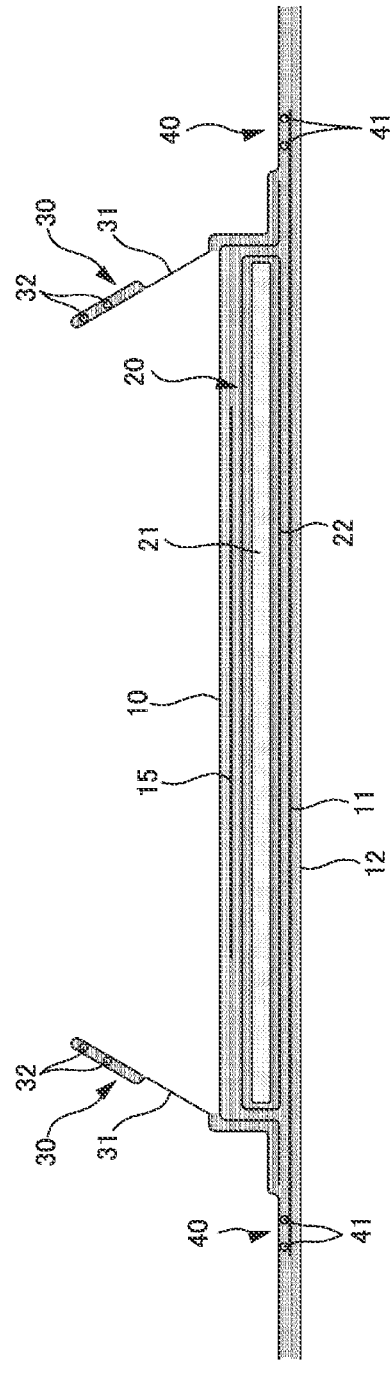

[FIG.4]
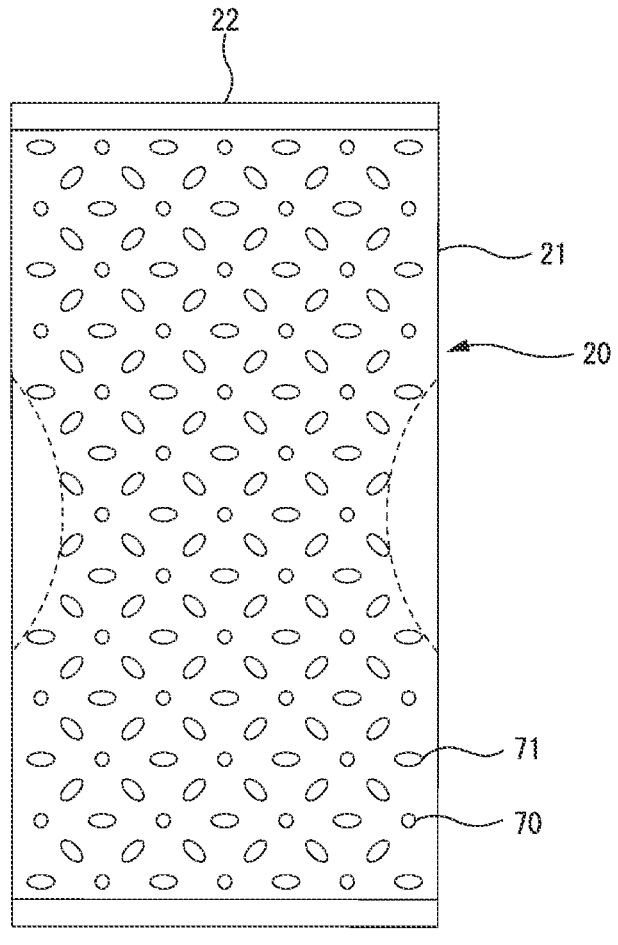

[FIG.5]
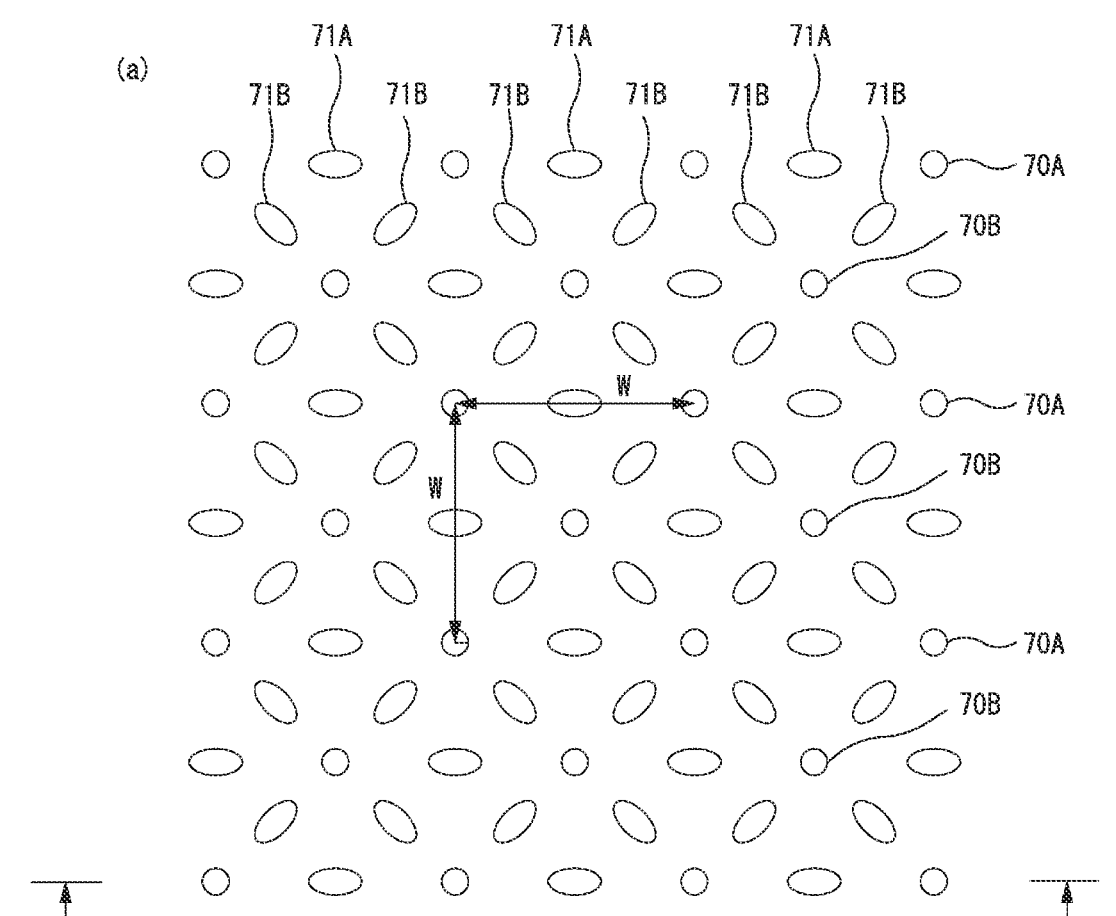
(a)
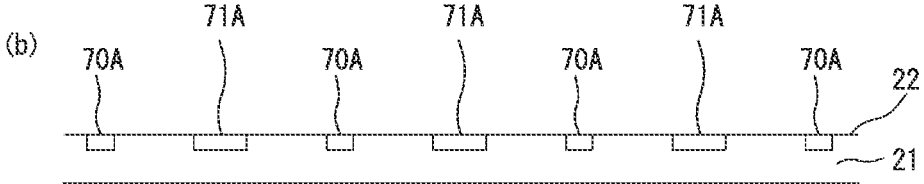
(b)

[FIG.6]
(b)
(d)
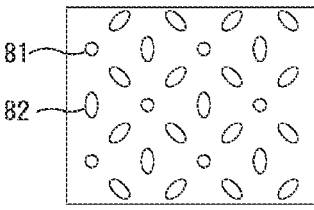
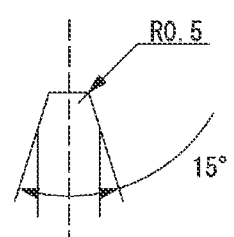
(a)
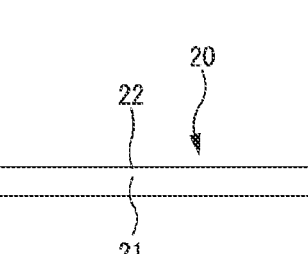
(c)

[FIG.7]
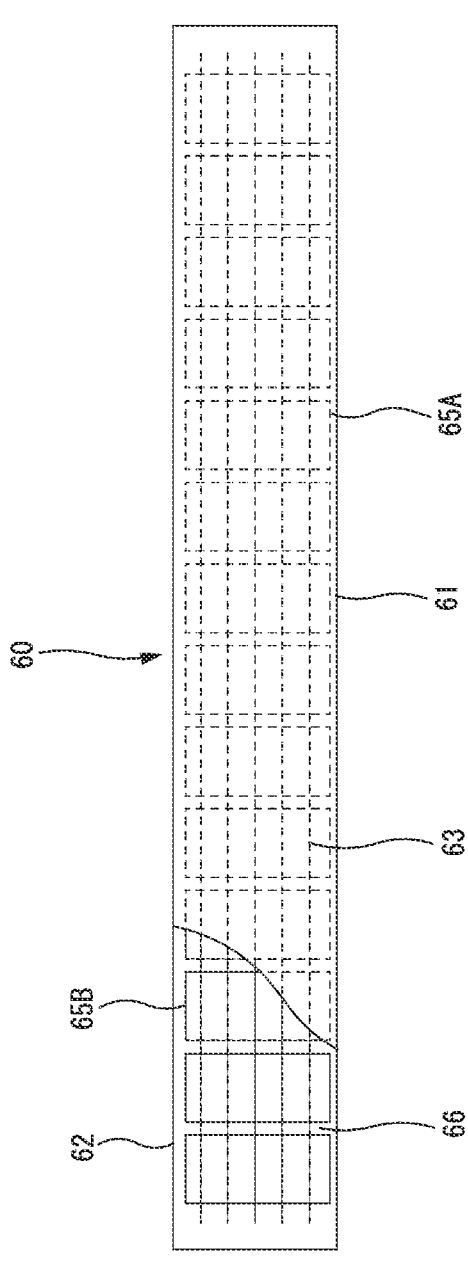

[FIG.8]
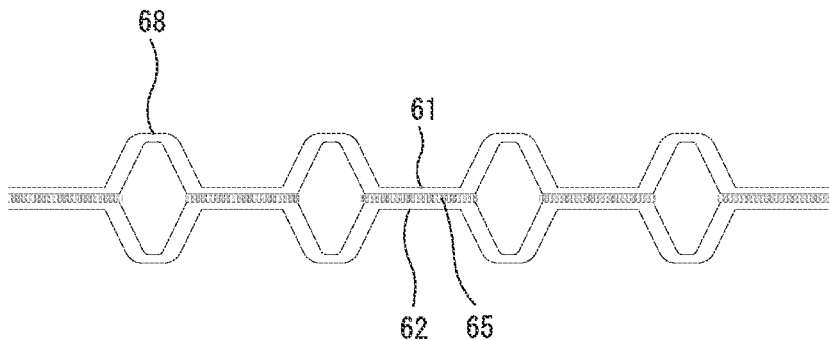

DISPOSABLE DIAPER AND METHOD FOR MANUFACTURING SAME

CROSS-REFERENCE TO RELATED APPLICATIONS

This application is the U.S. national stage application of International Application PCT/JP2022/009453, filed Mar. 4, 2022, which international application was published on Nov. 24, 2022, as International Publication WO 2022/244386 in the Japanese language. The International Application claims priority of Japanese Patent Application No. 2021-085134, filed May 20, 2021. The international application and Japanese application are both incorporated herein by reference, in entirety.

FIELD OF ART

The present invention relates to disposable diapers and a method for manufacturing the same, in particular, to disposable diapers of which absorber body of an absorbent element is kept from distortion or deformation, and changes its shape to the motion of the wearer to provide enhanced fitting and wearing comfort, and a method for manufacturing the same.

BACKGROUND ART

There is known a technique for enhancing fitting or the like properties of disposable diapers, by providing, on the body side of the absorber body via a wrapping sheet, a plurality of linear compressed areas arranged at intervals in the width direction, each extending in the front-back direction, and a plurality of dotted compressed areas between adjacent linear compressed areas (Patent Publication 1).

PRIOR ART PUBLICATION

Patent Publication

Patent Publication 1: JP 2012-179220 A

SUMMARY OF THE INVENTION

Problem to be Solved by the Invention

According to the technique taught in Patent Publication 1, however, the absorber body, having high rigidity, may not change its shape to the motion of the wearer. Further, the wrapping sheet on which the linear compressed areas and the dotted compressed areas are densely provided is liable to tear, through which the adhesive, such as a hot melt adhesive, is exposed and adhered to the manufacturing equipment, such as rollers, so that the production line may need to be stopped in order to remove the adhered adhesive, which deteriorates productivity.

It is therefore an object of the present invention to provide a disposable diaper of which absorber body changes its shape to the motion of the wearer to provide enhanced fitting and wearing comfort, without excessive increase in rigidity of the absorber body, and to provide a method for manufacturing a disposable diaper excellent in fitting and wearing comfort, at an improved production efficiency, by which tearing of the wrapping sheet may be prevented.

Means for Solving the Problem

Means for solving the above problems are as follows.

The first means is characterized in that it includes a liquid-pervious top sheet, a liquid-impervious backing sheet, and an absorbent element interposed therebetween, the absorbent element including an absorber body for absorbing bodily waste, and a wrapping sheet wrapping an outer periphery of the absorber body, wherein round compressed areas devoid of straight or angular part and oval compressed areas devoid of straight or angular part is provided on the body side of the absorbent element, wherein the round compressed areas include first round compressed areas arranged at intervals in a width direction and a front-back direction of the diaper, wherein the round compressed areas further include second round compressed areas arranged at the intervals in the width direction and the front-back direction of the diaper, shifted from the first round compressed areas by half the intervals in the width direction and the front-back direction, wherein the oval compressed areas include first oval compressed areas, each arranged at a center between first round compressed areas adjacent to each other in the width direction or at a center between second round compressed areas adjacent to each other in the width direction, with a major axis of each first oval compressed area being aligned to the width direction, and wherein the oval compressed areas further includes second oval compressed areas, each arranged at a center between a first round compressed area and a second round compressed area adjacent thereto in the width and front-back directions, with a major axis of the second oval compressed area being aligned to a virtual line connecting the first round compressed area and the second round compressed area adjacent thereto in the width and front-back directions.

The second means is characterized in that, in the first means, the first and second round compressed areas have a diameter of 1 to 3 mm, and the first and second oval compressed areas have a minor axis of 1 to 3 mm long and a major axis is 3 to 5 mm long.

The third means is characterized in that, in the first or second means, each of the intervals is 12 to 24 mm.

The fourth means is characterized in that, in any one of the first to third means, a dent depth of the first and second round compressed areas is 0.25 to 1.00 mm, and a dent depth of the first and second oval compressed areas is 0.25 to 1.00 mm.

The fifth means is, in a method for manufacturing a disposable diaper including a liquid-pervious top sheet, a liquid-impervious backing sheet, and an absorbent element interposed therebetween, the absorbent element including an absorber body for absorbing bodily waste, and a wrapping sheet wrapping an outer periphery of the absorber body, wherein the absorbent element is provided on its body side round compressed areas devoid of straight or angular part and oval compressed areas devoid of straight or angular part, characterized in that the method includes a first step of wrapping the absorber body with the wrapping sheet via an adhesive to obtain an unworked absorbent element, and a second step of passing the unworked absorbent element obtained from the first step between an upper roller and a lower roller so as to make a thickness in a top-bottom direction into a predetermined compressed thickness, wherein the upper roller has on its roll surface round protrusions for forming round compressed areas and oval protrusions for forming oval compressed areas, and wherein the predetermined compressed thickness is 0.5 to 1.2 mm.

The sixth means is characterized in that, in the fifth means, outer peripheral ends of the round protrusions and the oval protrusions are round chamfered with a particular radius.

The seventh means is characterized in that, in the fifth or sixth means, the roll surface of the upper roller is coated with a silicone-based material.

Effect of the Invention

According to the first means, the disposable diaper includes a liquid-pervious top sheet, a liquid-impervious backing sheet, and an absorbent element interposed therebetween, the absorbent element including an absorber body for absorbing bodily waste, and a wrapping sheet wrapping the outer periphery of the absorber body, wherein the absorbent element is provided on its body side round compressed areas devoid of straight or angular part and oval compressed areas devoid of straight or angular part, wherein the round compressed areas include first round compressed areas arranged at intervals in a width direction and a front-back direction of the diaper, wherein the round compressed areas further include second round compressed areas arranged at the intervals in the width direction and the front-back direction of the diaper, shifted from the first round compressed areas by half the intervals in the width direction and the front-back direction, wherein the oval compressed areas include first oval compressed areas, each arranged at the center between first round compressed areas adjacent to each other in the width direction or at the center between second round compressed areas adjacent to each other in the width direction, with the major axis of each first oval compressed area being aligned to the width direction, and wherein the oval compressed areas further include second oval compressed areas, each arranged at the center between a first round compressed area and a second round compressed area adjacent thereto in the width and front-back directions, with the major axis of the second oval compressed area being aligned to a virtual line connecting the first round compressed area and the second round compressed area adjacent thereto in the width and front-back directions. Accordingly, the absorber body may change its shape easily in the front-back direction and the width direction, to the motion of the wearer to provide enhanced fitting and wearing comfort of the diaper. Further, the rigidity of the absorber body may be enhanced, though not excessively, to keep the absorber body from distortion, deformation, or the like.

According to the second means, the first and second round compressed areas have a diameter of 1 to 3 mm, and the first and second oval compressed areas have the minor axis of 1 to 3 mm long and the major axis of 3 to 5 mm long. Accordingly, in addition to the effect from the first means, the wrapping sheet may wrap the outer periphery of the absorber body without tearing or being excessively thinned. Further, the rigidity of the absorber body may be enhanced without excessively hardening, to further keep the absorber body from distortion, deformation, or the like.

According to the third means, each of the intervals is 12 to 24 mm. Accordingly, in addition to the effect from the first or second means, the rigidity of the absorber body may be enhanced without excessively hardening, to still further keep the absorber body from distortion, deformation, or the like.

According to the fourth means, a dent depth of the first and second round compressed areas is 0.25 to 1.00 mm, and a dent depth of the first and second oval compressed areas is 0.25 to 1.00 mm. Accordingly, in addition to the effect from any one of the first to third means, tearing or excessive thinning of the wrapping sheet may further be prevented.

According to the fifth means, in a method for manufacturing a disposable diaper including a liquid-pervious top sheet, a liquid-impervious backing sheet, and an absorbent element interposed therebetween, the absorbent element including an absorber body for absorbing bodily waste, and a wrapping sheet wrapping the outer periphery of the absorber body, wherein round compressed areas devoid of straight or angular part and oval compressed areas devoid of straight or angular part is provided on the body side of the absorbent element, the method includes a first step of wrapping the absorber body with the wrapping sheet via an adhesive to obtain an unworked absorbent element, and a second step of passing the unworked absorbent element obtained from the first step between an upper roller and a lower roller so as to make the thickness in the top-bottom direction into a predetermined compressed thickness, wherein the upper roller has on its roll surface round protrusions for forming round compressed areas and oval protrusions for forming oval compressed areas, and wherein the predetermined compressed thickness is 0.5 to 1.2 mm. Accordingly, tearing or the like of the wrapping sheet may be prevented to keep the adhesive, such as a hot melt adhesive, joining the absorber body and the wrapping sheet, from leaking to thereby improve productivity.

According to the sixth means, the outer peripheral ends of the round protrusions and the oval protrusions are round chamfered with a particular radius. Accordingly, in addition to the effect from the fifth means, tearing or the like of the wrapping sheet may further be prevented.

According to the seventh means, the roll surface of the upper roller is coated with a silicone-based material. Accordingly, in addition to the effect from the fifth or sixth means, tearing or the like of the wrapping sheet may further be prevented.

BRIEF DESCRIPTION OF THE DRAWINGS

FIG. 1 is a plan view of a disposable diaper on its body side.

FIG. 2 is a plan view of the disposable diaper on its side opposite from the body side.

FIG. 3 is a cross sectional view taken along lines A-A in FIG. 1.

FIG. 4 is a plan view of the absorbent element.

FIG. 5(a) is a partially enlarged plan view of FIG. 4, and FIG. 5(b) is a cross sectional view taken along lines A-A in FIG. 5(a).

FIG. 6(a) illustrates how to manufacture the absorbent element, FIG. 6(b) is a plan view of the upper roller, FIG. 6(c) is a plan view of the lower roller, and FIG. 6(d) illustrates the outer peripheral end of a round protrusion.

FIG. 7 is a plan view of a stretchable sheet.

FIG. 8 is an explanatory view of the profile of the ridges of the stretchable sheet.

MODES FOR CARRYING OUT THE INVENTION

Referring to FIGS. 1 to 3, the disposable diaper is composed of a liquid-pervious top sheet 10 arranged on the body side, a liquid-impervious backing sheet 11 arranged on the side opposite from the body side, and an absorbent element 20 interposed between the top sheet 10 and the backing sheet 11.

The body-side surface of the top sheet 10 is preferably coated with a hydrophilizer in advance. In this way, urine or the like excreted onto the top sheet 10 may be migrated into the absorbent element 20 so as not to leak outside. The absorbent element 20 is composed of an absorber body 21 and a wrapping sheet 22 wrapping the absorber body 21.

As shown in FIG. 4, on the body side of the absorber body 21 and the wrapping sheet 22 are provided round compressed areas 70 each in a circular shape devoid of straight or angular part and oval compressed areas 71 each in an elliptical shape devoid of straight or angular part, and the round compressed areas 70 and the oval compressed areas 71 are arranged uniformly all over without biasing toward one side. In this way, tearing of the wrapping sheet 22 may be prevented, and the absorber body 21 may be kept from distortion, deformation, or the like. Also, loss of shape of the absorber body 21 into which liquid, such as excreted urine, has been absorbed, may be avoided. Further, as the body side of the absorber body 21 and the wrapping sheet 22 are provided on the body side with the round compressed areas 70 and the oval compressed areas 71 uniformly distributed all over, the excreted liquid is diffused all over in the width direction and the front-back direction of the absorber body 21 and absorbed, so that the so-called wet back, by which the liquid absorbed in the absorber body 21 returns back through the wrapping sheet 22 to the top sheet 10, may be avoided. It is indisputable that, according to the present invention, the round compressed areas 70 and the oval compressed areas 71 are provided on the body side of the absorber body 21 and the wrapping sheet 22, but may also be provided on the side opposite from the body side of the absorber body 21 and the wrapping sheet 22.

As shown in FIG. 5(a), round compressed areas (first round compressed areas in the claims) 70A are arranged at predetermined intervals W in the width direction and the front-back direction. Round compressed areas (second round compressed area in the claims) 70B are arranged at the predetermined intervals W in the width direction and the front-back direction, shifted from the round compressed areas 70A by half the interval W in the width direction and the front-back direction.

Oval compressed areas (first oval compressed areas in the claims) 71A are each arranged at the center between round compressed areas 70A adjacent to each other in the width direction or at the center between round compressed areas 70B adjacent to each other in the width direction, with the major axis of each oval compressed area 71A being aligned to the width direction. In this way, the absorber body 21 may readily curve in the front-back direction along the oval compressed areas 71A, which enhances fitting and wearing comfort of the disposable diaper.

Oval compressed areas (second compressed areas in the claims) 71B are each arranged at the center between a round compressed area 70A and a round compressed area 70B adjacent thereto in the width and front-back directions, with the major axis of each oval compressed area 71b being aligned to the virtual line connecting the round compressed area 70A and the round compressed area 70B adjacent thereto in the width and front-back directions. In this way, the absorber body 21 may readily curve in the width direction along the oval compressed areas 71B, which enhances fitting and wearing comfort of the disposable diaper.

It is preferred that the round compressed areas 70A and round compressed areas 70B have a diameter of 1 to 3 mm, and the oval compressed areas 71A and the oval compressed areas 71B have a minor axis of 1 to 3 mm long, and the major axis of 3 to 5 mm long. In this way, tearing of the wrapping sheet 22 may be prevented, and rigidity of the absorber body 21 may be enhanced, though not excessively, to keep it from deformation. Further, during manufacture of the absorbent element 20, the adhesive, such as a hot melt adhesive, applied to the body side of the absorber body 21 may be kept from leaking through the excessively thinned wrapping sheet 22, onto the body side thereof.

Each interval W may preferably be 12 to 24 mm, the area occupancy of the round compressed areas 70A and the round compressed areas 70B may preferably be 0.5 to 5%, and the area occupancy of the oval compressed areas 71A and the oval compressed areas 71B may preferably be 5 to 30%. In this way, rigidity of the absorber body 21 may be enhanced without excessively hardening, to further keep the absorber body 21 from deformation.

Referring to FIG. 5(b), the dent depth of the round compressed areas 70A and the round compressed areas 70B may preferably be 0.25 to 1.00 mm and, similarly, the dent depth of the oval compressed areas 71A and the oval compressed areas 71B may preferably be 0.25 to 1.00 mm. In this way, tearing of the wrapping sheet 22 may further be prevented. Further, during manufacture of the absorbent element 20, the adhesive, such as a hot melt adhesive, applied to the body side of the absorber body 21 may be kept from leaking through the excessively thin wrapping sheet 22, on the body side thereof.

In this embodiment, the round compressed areas 70A and the round compressed areas 70B have the diameter of 2 mm, the intervals W in the width direction and the front-back direction is each in 18 mm, and the area occupancy of the round compressed areas 70A and the round compressed areas 70B is about 2%. The oval compressed areas 71A and the oval compressed areas 71B have the minor axis of 2 mm long, and the area occupancy of the oval compressed areas 71A and the oval compressed areas 71B is about 12%. Note that, as used herein, the round compressed areas 70A and the round compressed areas 70B are collectively referred to as round compressed areas 70, and the oval compressed areas 71A and the oval compressed areas 71B are collectively referred to as oval compressed areas 71.

<Manufacture of Absorbent Element>

Referring to FIG. 6(a), first, the outer periphery of the absorber body 21 is wrapped with the wrapping sheet 2 to obtain an unworked absorbent element 23. Note that the absorber body 21 and the wrapping sheet 22 are joined with an adhesive, such as a hot melt adhesive.

Next, it is preferred to pass the unworked absorbent element 23 between a pair of upper and lower rollers to compress the unworked absorbent element 23 in the top-bottom direction to obtain an absorbent element 20 having a thickness in the top-bottom direction of 0.5 to 1.2 mm. In this way, loss of shape of the absorber body 21 into which liquid, such as urine, has been absorbed, may further be avoided.

As shown in FIG. 6(b), the roll surface of the upper roller 80 facing the body side of the unworked absorbent element 23 is provided with round protrusions 81 for forming the round compressed areas 70 and oval protrusions 82 for forming the oval compressed areas 71.

Referring to FIG. 6(c), the roll surface of the lower roller 83 facing the side opposite from the body side of the unworked absorbent element 23 is neither provided with round protrusions 81 nor oval protrusions 82 and flat.

Referring to FIG. 6(d), the outer peripheral ends of the round protrusions 81 and the oval protrusions 82 are round chamfered with a particular radius. In this way, tearing of the wrapping sheet 22 may be prevented to keep the adhesive from leaking through the tears in the wrapping sheet and adhering onto the outer periphery of the round protrusions 81 and the oval protrusions 82 of the upper roller 80. Note that the roll surfaces of the upper roller 80 and the lower roller 83 may preferably be coated with a silicone-based material. In this way, tearing of the wrapping sheet 22 may further be prevented.

In the present embodiment, the thickness in the top-bottom direction of the unworked absorbent element 23 is 4 to 8 mm, and the unworked absorbent element 23 is compressed between the upper roller 80 and the lower roller 83, so that the thickness of the resulting absorbent element 20 is about 3 to 7 mm. The dent depth of the round compressed areas 70A and the round compressed areas 70B is 0.25 to 1.00 mm and, similarly, the dent depth of the oval compressed areas 71A and the oval compressed areas 71B is 0.25 to 1.00 mm.

Referring to FIGS. 1 to 3, on the side of the backing sheet 11 opposite from the body side is provided an exterior sheet 12. It is preferred to interpose an intermediate sheet 15 between the top sheet 10 and the absorbent element 20, which causes the bodily waste passing through the top sheet 10 to migrate into the absorbent element 20 to prevent backflow of the bodily waste.

On the lateral portions opposed in the width direction of the absorbent element 20, at a predetermined distance therefrom, a pair of three-dimensional gather parts 30 are provided for keeping the bodily waste from leaking outside. Each three-dimensional gather part 30 is composed of a gathered sheet 31 substantially continuous in the front-back direction, and elongate elastic members 32 fixed to the gathered sheet 31 in a stretched state in the front-back direction.

Laterally outwards of fold lines 30A of the pair of three-dimensional gather parts 30, at a predetermined distance therefrom, a pair of planar gathers 40 are provided for keeping discharged urea from leaking outside. The planar gathers 40 are formed with elongate elastic members 41 fixed in a stretched state along the front-back direction between the backing sheet 11 and the gathered sheet 31.

It is preferred to form each three-dimensional gather part 30 such that the dimension L1 in the width direction of the gathered sheet 31 between the edge and the folded line 30A of the three-dimensional gather part 30 is the same as the dimension L2 in the width direction of the gathered sheet 31 between the folded line 30A and the lateral edge of the gather part 30. In this way, the three-dimensional gather parts 30 may be folded onto the body side of the top sheet 10 to allow application of a hydrophilizer over a wide range of the top sheet 10. During the application of the hydrophilizer to the top sheet 10, lowering of water-repelling property of the three-dimensional gather parts 30, which may be caused by application of the hydrophilizer, can be prevented.

In the opposed ends in the front-back direction of the absorbent element 20, a pair of end flaps EF is formed, while in the opposed sides in the width direction of the absorbent element 20, a pair of side flaps SF is formed.

On the side flaps SF on the opposed sides in the width direction in the dorsal section are provided a pair of fastening tapes 50. Each fastening tape 50 is composed of a base member 51 fixed to the side flap SF, and an engaging part 52 provided on the body side of the base member 51.

On the surface of the exterior sheet 12 opposite from the body side, a rectangular target sheet 55 is provided in the ventral section, which extends in the width direction for a predetermined extent in the front-back direction, and on which the engaging parts 52 of the fastening tapes 50 are to engage.

Between the top sheet 10 and the backing sheet 11 forming the dorsal end flap EF, a stretchable sheet 60 to be discussed later is disposed.

As shown in FIG. 7, the stretchable sheet 60 is composed of an inner sheet 61 facing the top sheet 10, an outer sheet 62 facing the backing sheet 11, and elongate stretchable members 63 fixed in a stretched state along the width direction between the inner sheet 61 and the outer sheet 62.

The stretchable members 63 are fixed to first rectangular bonding zones 65A formed on the side of the inner sheet 61 opposite from the body side at intervals in the width direction, and to second bonding zones 65 formed on the body side of the outer sheet 62 at intervals in the width direction. In this way, as shown in FIG. 8, ridges 68 with angle profile are formed on the body side and on the side opposite from the body side of the stretchable sheet 60, which causes the disposable diaper to fit on the dorsal waist region of the wearer. The first bonding zones 65A and the second bonding zones 65B may be formed through application of a hot melt adhesive. Note that, as used herein, the first boding zones 65A and the second bonding zones 65B are collectively referred to as bonding zones 65, and portions between adjacent bonding zones 65 are referred to as non-bonding portions 66.

Alternatively, instead of forming the bonding zones 65 on the inner sheet 61 and the outer sheet 62, bonding zones 65 may be formed on the outer surface of the stretchable members 63 at intervals in the width direction corresponding to the non-bonding portions 66 as discussed above to fix the inner sheet 61 and the outer sheet 62 to the stretchable members 63.

As used herein, the ventral section of the top sheet 10 refers to a portion covering 10 to 30% of the length of the top sheet 10 in the front-back direction from the ventral end of the top sheet 10 toward the dorsal side thereof, the intermediate section of the top sheet 10 refers to 40 to 80% of the length of the top sheet 10 in the front-back direction between the dorsal end of the ventral section and the ventral end of the dorsal section of the top sheet 10, and the dorsal section of the top sheet 10 refers to 10 to 30% of the length of the top sheet 10 in the front-back direction from the dorsal end of the top sheet 10 toward the ventral side thereof.

Next, materials and features of the top sheet 10 or the like will now be explained in turn.

<Top Sheet>

The top sheet 10 is formed of perforated or imperforated nonwoven fabric, porous plastic sheet, or the like. Among these, nonwoven fabric is not particularly limited in its raw material fibers. For example, synthetic fibers, such as polyolefin-based including polyethylene or polypropylene, polyester-based, or polyamide-based fibers, recycled fibers, such as rayon or cupra, natural fibers, such as cotton, or mixed fibers or composite fibers of two or more of these may be used. Further, the nonwoven fabric may have been produced through any processing. The processing may include known processes, such as spunlacing, spunbonding, thermal bonding, melt-blowing, needle punching, air through, and point bonding. For example, when flexibility or draping properties are required, spunlacing is preferred, whereas when bulkiness or softness is required, thermal bonding is preferred.

Note that the surface of the top sheet 10 is preferably provided with a hydrophilizer applied in advance.

<Backing Sheet>

The backing sheet 11 is formed of a polyolefin-based resin, such as polyethylene or polypropylene, laminated nonwoven fabric having nonwoven fabric laminated over a polyethylene sheet or the like, or nonwoven fabric having a waterproof film interposed therein to substantially secure liquid-impermeability (in this case, the backing sheet 11 is composed of the waterproof film and the nonwoven fabric). It is indisputable that, other than these, liquid-impervious, moisture-permeable materials may also be used which are preferably used for preventing dampness recently. A sheet of such a liquid-impervious, moisture-permeable material may be a microporous sheet obtained by kneading an inorganic filler in a polyolefin-based resin, such as polyethylene or polypropylene, forming the resulting mixture into a sheet, and then uni- or biaxially drawing the sheet. Also, nonwoven fabric of microdenier fibers, or sheets that have been rendered liquid-impervious without using waterproof film through a process, such as enhancement of leak proof property by applying heat or pressure to minimize interfiber gaps, or coating with a highly water-absorbable resin or a hydrophobic resin or water repellent, may be used as the backing sheet 11.

<Exterior Sheet>

The exterior sheet 12 is for supporting and fitting the absorbent element 20 on a wearer. The exterior sheet 12 is shaped like an hourglass having its middle portion in the front-back direction narrowed on the opposed lateral sides, with which the legs of the wearer are surrounded.

The exterior sheet 12 is preferably formed of nonwoven fabric. The type of the nonwoven fabric is not particularly limited, and its raw material fibers may be synthetic fibers, such as polyolefin-based including polyethylene or polypropylene, polyester-based, or polyamide-based fibers, recycled fibers, such as rayon or cupra, or natural fibers, such as cotton. The nonwoven fabric may have been processed by spunlacing, spunbonding, thermal bonding, air through, needle punching, or the like process. Among these, continuous fiber nonwoven fabric, such as spunbonded nonwoven fabric, SMS nonwoven fabric, SMMS nonwoven fabric, or the like are preferred for reconciling texture and strength. One or a plurality of sheets in a stack of nonwoven fabric may be used. In the latter case, sheets of nonwoven fabric may preferably be bonded with an adhesive or the like. The nonwoven fabric, when used, may preferably has a fiber basis weight of 10 to 50 g/m$^2$, particularly 15 to 30 g/m$^2$.

<Intermediate Sheet>

The intermediate sheet 15 is formed of a material similar to the one for the top sheet 10. The intermediate sheet 15 is preferably joined to the top sheet 10 and, when joined by heat embossing or ultrasonic melt-bonding, preferably made of a material having a melting point similar to that of the top sheet 10. When the intermediate sheet 15 is formed of nonwoven fabric, the fineness of the fibers of the nonwoven fabric may preferably be about 2.0 to 7.0 dtex.

<Absorber Body>

The absorber body 21 may be formed of an assembly of fibers. Such an assembly of fibers may be an accumulation of discontinuous fibers of fluff pulp, synthetic fibers, or the like, as well as an assembly of filaments obtained by opening, where necessary, a tow (fiber bundle) of synthetic fibers, such as cellulose acetate. The fiber basis weight may be about 100 to 300 g/m$^2$ for an accumulation of fluff pulp or discontinuous fibers, and about 30 to 120 g/m$^2$ for an assembly of filaments. The fineness of the synthetic fibers, when used, is, for example, 1 to 16 dtex, preferably 1 to 10 dtex, more preferably 1 to 5 dtex. In an assembly of filaments, the filaments may be of uncrimped fibers, but crimped fibers are preferred. The number of crimps of the crimped fibers may be, for example, 5 to 75, preferably 10 to 50, more preferably about 15 to 50 per inch. Uniformly crimped fibers are often used.

The absorber body 21 preferably contains superabsorbent polymer particles, and in particular, preferably has superabsorbent polymer particles (SAP particles) dispersed with respect to the assembly of fibers substantially all over its thickness, at least in the liquid-receiving area.

The SAP particles, when absent or present only in a slight amount in the top, bottom, or middle portion of the absorbent body 21, cannot be said as being "dispersed substantially all over its thickness". The phrase "dispersed substantially all over its thickness" encompasses not only an embodiment wherein the SAP particles are dispersed "homogenously" with respect to the assembly of fibers all over the thickness, but also an embodiment wherein the SAP particles are "unevenly distributed" in the top, bottom, and/or middle portion, yet dispersed in each of the top, bottom, and middle portion. Further, embodiments are not excluded wherein part of the SAP particles remain on the surface of the fiber assembly without intruding therein, or pass through the fiber assembly to rest on the wrapping sheet 22.

The superabsorbent polymer particles include not only "particles" but also "powders". The particle size of the superabsorbent polymer particles may be the one used in this type of absorbent articles as it is, and may preferably be 1000 μm or smaller, particularly preferably 150 to 400 μm. Any material of the superabsorbent polymer particles may be used without particular limitation, and those having a water absorption of 40 g/g or more are preferred. The superabsorbent polymer particles may be of starch-based, cellulose-based, or synthetic polymer-based, and starch-acrylic acid (salt) graft copolymers, saponified products of starch-acrylonitrile copolymers, cross-linked sodium carboxymethyl cellulose, or acrylic acid (salt) polymers may be used. The superabsorbent polymer particles may preferably be in ordinary powder or granular form, but particles in other forms may also be used.

The superabsorbent polymer particles having a water absorption rate of 70 seconds or less, particularly 40 seconds or less, may preferably be used. With too low a water absorption rate, so-called back flow may likely to occur, wherein liquid supplied into the absorber body 21 returns out of the absorber body 21.

The basis weight of the superabsorbent polymer particles may suitably be decided depending on the amount of absorption required in an intended use of the absorber body 21. Thus, it depends, but the basis weight may be 50 to 350 g/m$^2$. With a polymer basis weight of less than 50 g/m$^2$, the amount of absorption may hardly be acquired. A basis weight over 350 g/m$^2$ not only saturates the effect, but also causes grainy discomfort due to excessive amount of the superabsorbent polymer particles.

<Wrapping Sheet>

The wrapping sheet 22 may be formed of tissues, in particular, crepe paper, nonwoven fabric, polyethylene-laminated nonwoven fabric, perforated sheet, or the like, provided that preferably the sheet will not allow escape of the superabsorbent polymer particles. When nonwoven fabric is used in place of crepe paper, hydrophilic SMMS (spunbonded/melt-blown/melt-blown/spunbonded) nonwoven fabric is particularly preferred, which may be made of polypropylene, polyethylene/polypropylene, or the like. The fiber basis weight is preferably 5 to 40 g/m$^2$, particularly 10 to 18 g/m$^2$.

<Three-Dimensional Gather Part>

The gathered sheets 31 of the three-dimensional gather parts 30 may be formed of water-repellent nonwoven fabric, and the elastic members 32 may be formed of rubber threads or the like. A plurality of the elastic members may be provided on each gather part, or only one elastic member may be provided on each gather part.

Each gathered sheet 31 has a starting edge for widthwise joining on a lateral side portion of the top sheet 10, and the surface of the gathered sheet 31 opposite from the body side in the portion outwards in the width direction of this joining edge is bonded to a lateral side portion of the backing sheet 11 and a lateral side portion of the exterior sheet 12 located outwards thereof in the width direction, with a hot melt adhesive or the like.

In the round-leg areas, each three-dimensional gather part 30 inwards in the width direction of the joining starting edge is fixed to the top sheet 10 at both end portions in the product front-back direction, while the portion between these end portions of the gather part is a non-fixed free portion, which stands up under the contracting force of the elastic members 32. The diaper, when worn, takes a vessel-like shape to fit on the body while the contracting force of the elastic members 32 acts, so that the three-dimensional gather parts 30 stand up under the contracting force of the elastic members 32 to be brought into close contact onto the legs. As a result, so-called side leakage around the legs may be kept from occurring.

<Planar Gathers>

Between the gathered sheet 31 and the backing sheet 11, round-leg elastic members 41, such as rubber threads, are fixed stretched in the front-back direction. A plurality of the round-leg elastic members 41 may be provided on each side, or only one elastic member may be provided on each side.

<Fastening Tape>

The base member 51 of each fastening tape 50 in its basal portion is fixed between the gathered sheet 31 and the exterior sheet 12 with a hot melt adhesive or the like. The base member 51 is formed of nonwoven fabric, plastic film, polyethylene-laminated nonwoven fabric, paper, or a composite material thereof.

The engaging part 52 is formed of a hook member of a mechanical fastener. The hook member has a number of engaging projections on its outer surface, and the engaging projections may be in (A) tick-shaped, (B) J-shaped, (C) mushroom-shaped, (D) T-shaped, or (E) double J-shaped (wherein J-shaped parts are joined back to back), and any shape may be employed. It is indisputable that the engaging part of the fastening tape 50 may be a pressure-sensitive adhesive layer.

<Target Sheet>

The target sheet 55 is formed of plastic film, nonwoven fabric, or the like, having a multitude of thread loops on its surface.

<Stretchable Sheet>

The stretchable sheet 60 is for contracting the dorsal end flap EF to bring the same into close contact with the back of the wearer. As shown in FIG. 7, the stretchable sheet 60 is composed of the inner sheet 61 formed of nonwoven fabric, the outer sheet 62 formed of nonwoven fabric, and a plurality of elongate stretchable members 63 arranged at intervals in the front-back direction between the inner sheet 61 and the outer sheet 62, each of the stretchable members 63 extending in the width direction. Each of the stretchable members 63 is a rubber thread having a fineness of 470 to 620 dtex and arranged stretched at a stretch rate of 200 to 250%.

The lateral portions opposed in the width direction of the stretchable sheet 60 are located in the vicinity of the lateral portions opposed in the width direction of the pair of gathered sheets, while the lateral portions opposed in the width direction of the stretchable members 63 are located in the lateral portions opposed in the width direction of the backing sheet 11.

<Explanation of Terms in the Specification>

The following terms appearing in the present specification shall have the following means unless otherwise specified herein.

The "front-back (longitudinal) direction" refers to the direction connecting the ventral side (front side) and the dorsal side (back side), whereas the "width direction" refers to the direction orthogonal to the front-back direction (right-left direction).

The "top side" refers to the side of a disposable diaper, when worn, closer to the skin of the wearer, whereas the "underside" refers to the side of a disposable diaper, when worn, away from the skin of the wearer. The "top face" refers to the face of a member of a disposable diaper, when worn, closer to the skin of the wearer, whereas the "under face" refers to the face of a disposable diaper, when worn, away from the skin of the wearer.

The "MD" and "CD" refer to the flow direction (MD: machine direction) and the lateral direction orthogonal thereto (CD: cross direction) in the production facilities, respectively, and either one of these is aligned to the front-back direction of the product while the other is aligned to the width direction of the product. The MD of nonwoven fabric is the direction of fiber orientation in the nonwoven fabric. The fiber orientation refers to the direction along which the fibers of the nonwoven fabric are aligned, and may be identified, for example, by a measurement method pursuant to the fiber orientation testing method using zero-span tensile strength prescribed in TAPPI Standard Method T471, or by a simplified measurement method for determining the fiber orientation by the ratio of tensile strengths in the front-back direction and in the width direction.

The "spread state" refers to the state in which a disposable diaper is spread flatly without contraction or slack.

The "stretch rate" refers to a value with respect to the natural length being 100%. For example, a 200% stretch rate is synonymous with stretch in two folds.

The "gel strength" is determined as follows. To 49.0 g of artificial urine, 1.0 g of superabsorbent polymer is added and stirred with a stirrer. The resulting gel is left in a chamber with constant temperature and humidity at 40° C. at 60% RH for 3 hours, and then the temperature is returned to the ordinary temperature. The gel strength is measured in a curd meter (Curdmeter-MAX ME-500 manufactured by I. techno Engineering).

The "artificial urine" is a mixture of 2 wt % urea, 0.8 wt % sodium chloride, 0.03 wt % calcium chloride dihydrate, 0.08 wt % magnesium sulfate heptahydrate, and 97.09 wt % ion-exchanged water, and is used at 40° C. unless otherwise specified herein.

The "basis weight" is determined as follows. A specimen or test piece is preliminarily dried, left in a laboratory or in apparatus under the standard conditions (23±1° C. temperature and 50±2% relative humidity in the testing location) until constant mass is attained. The preliminary drying refers to attaining constant mass from a specimen or test piece in the environment at a temperature of 100° C. No preliminary drying may be performed on fibers with an official regain of 0.0%. From the test piece of the constant mass, a specimen of 100 mm×100 mm size is cut out using a sampling template (100 mm×100 mm). The weight of the specimen is measured and multiplied by 100 times to calculate the weight per 1 m², which is taken as the basis weight.

The "thickness" is automatically measured using an automatic thickness meter (KES-G5 handy compression tester program) under a load of 0.098 N/cm² with the compression area of 2 cm².

The "water absorption" is determined in accordance with JIS K7223-1996 "Testing method for water absorption capacity of super absorbent polymers".

The "water absorption rate" is defined as the "time spent until the end point is reached" in carrying out JIS K7224-1996 "Testing method for water absorption rate of super absorbent polymers" using 2 g of superabsorbent polymer and 50 g of saline.

A test or measurement shall be, in the absence of description about environmental conditions, performed in a laboratory or in apparatus under the standard conditions (23±1° C. temperature and 50±2% relative humidity in the testing location).

The size of each part refers to the size not in the natural length state but in the spread state, unless otherwise specified.

INDUSTRIAL APPLICABILITY

The present invention is applicable to absorbent articles, such as disposable diapers.

DESCRIPTION OF REFERENCE SIGNS

10: top sheet
11: backing sheet
20: absorbent element
21: absorber body
22: wrapping sheet
70: round compressed area
70A: round compressed area (first round compressed area)
70B: round compressed area (second round compressed area)
71: oval compressed area
71A: oval compressed area (first oval compressed area)
71B: oval compressed area (second oval compressed area)
80: upper roller
81: round protrusion
82: oval protrusion
83: lower roller
W: interval

The invention claimed is:

1. A disposable diaper comprising:
a liquid-pervious top sheet;
a liquid-impervious backing sheet; and
an absorbent element interposed therebetween,
wherein the absorbent element comprising an absorber body for absorbing bodily waste, and a wrapping sheet wrapping an outer periphery of the absorber body, wherein round compressed areas devoid of straight or angular part and oval compressed areas devoid of straight or angular part areis provided on the body side of the absorbent element, wherein the round compressed areas comprises first round compressed areas arranged at first intervals in a width direction and a front-back direction of the diaper, wherein the round compressed areas further comprises second round compressed areas arranged at the first intervals in the width direction and the front-back direction of the diaper, wherein the second round compressed areas are spaced apart from the first round compressed areas by second intervals in the width direction and the front-back direction, wherein the second intervals are half the size of first intervals in the width direction and the front-back direction, wherein the oval compressed areas comprises first oval compressed areas, each arranged at a center between first round compressed areas adjacent to each other in the width direction or at a center between second round compressed areas adjacent to each other in the width direction, with a major axis of each first oval compressed area being aligned to the width direction, wherein the oval compressed areas further comprises second oval compressed areas, each arranged at a center between a first round compressed area and a second round compressed area adjacent thereto in the width and front-back directions, with a major axis of the second oval compressed area being aligned to a virtual line connecting the first round compressed area and the second round compressed area adjacent thereto in the width and front-back directions, and wherein an area occupancy of the round compressed areas is 0.5 to 5%, and an area occupancy of the oval compressed areas is 5 to 30%, with respect to a body-side surface of the absorbent element.

2. The disposable diaper according to claim 1, wherein the first and second round compressed areas have a diameter of 1 to 3 mm, and the first and second oval compressed areas have a minor axis of 1 to 3 mm long and a major axis of 3 to 5 mm long.

3. The disposable diaper according to claim 2, wherein each of the first intervals is 12 to 24 mm.

4. The disposable diaper according to claim 2, wherein a dent depth of the first and second round compressed areas is 0.25 to 1.00 mm, and a dent depth of the first and second oval compressed areas is 0.25 to 1.00 mm.

5. The disposable diaper according to claim 1, wherein each of the first intervals is 12 to 24 mm.

6. The disposable diaper according to claim 5, wherein a dent depth of the first and second round compressed areas is 0.25 to 1.00 mm, and a dent depth of the first and second oval compressed areas is 0.25 to 1.00 mm.

7. The disposable diaper according to claim 1, wherein a dent depth of the first and second round compressed areas is 0.25 to 1.00 mm, and a dent depth of the first and second oval compressed areas is 0.25 to 1.00 mm.

* * * * *